(12) United States Patent
Zhang et al.

(10) Patent No.: US 7,737,123 B2
(45) Date of Patent: Jun. 15, 2010

(54) MULTIDRUG RESISTANT ANTICANCER ANTHRACYCLINES

(75) Inventors: Guisheng Zhang, Columbus, OH (US); Lanyan Fang, Columbus, OH (US); Peng George Wang, Columbus, OH (US); Duxin Sun, Dublin, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 427 days.

(21) Appl. No.: 11/432,901

(22) Filed: May 12, 2006

(65) Prior Publication Data

US 2006/0276418 A1 Dec. 7, 2006

Related U.S. Application Data

(60) Provisional application No. 60/680,326, filed on May 12, 2005, provisional application No. 60/703,079, filed on Jul. 28, 2005, provisional application No. 60/706,688, filed on Aug. 9, 2005, provisional application No. 60/756,041, filed on Jan. 4, 2006.

(51) Int. Cl.
*A61K 31/70* (2006.01)
*C07H 15/24* (2006.01)

(52) U.S. Cl. .......................... 514/34; 536/6.4
(58) Field of Classification Search .................. 536/6.4
See application file for complete search history.

(56) References Cited

U.S. PATENT DOCUMENTS 5,532,218 A * 7/1996 Bargiotti et al. ............... 514/34
6,653,289 B1 11/2003 Animati et al.
6,673,907 B2 * 1/2004 Priebe et al. .................. 536/6.4

OTHER PUBLICATIONS

The Ohio State Univ. Research FNDN., Appln. No. PCT/US06/18630, filed May 12, 2006, International Search Report, Sep. 15, 2006.

Alper et al., "Metal Catalyzed Diazo Transfer for the Synthesis of Azides from Amines", Tetrahedron Letters, vol. 37, No. 34, pp. 6029-6032, 1996.
Arcamone et al., "Configurational Requirements of the Sugar Moiety for the Pharmacological Activity of Anthracycline Disaccharides", Biochemical Pharmacology vol. 57, pp. 1133-1139, 1999.
Caponigro et al., "A phase II study of sabarubicin (MEN-10755) as second line therap in patients with locally advanced or metasttic platinum/taxane resistant ovarian cancer", Investigational New Drugs, 23: 85-89, 2005.
Champoux, J.J., "DNA Topoisomerases: Structure, Function, and Mechanism", Annu. Rev. Biochem, 70: 369-413, 2001.
Ciesielska et al., "Cytotoxicity, cellular uptake and DNA damage by daunorubicin and its new analogues with modified daunosamine moiety", Cell Biology and Toxicology, 21: pp. 139-147, 2005.
Gewirtz, D.A., "A critical evaluation of the mechanisms of action proposed for the antitumor effects of the anthracycline antibiotics adriamycin and daunorubicin", Biochemical Pharmacology, vol. 57, pp. 727-741, 1999.
Lear, et al., "A Direct and efficient a-selective glycosylation protocol for the kedarcidin sugar, L-mycarose: AgPF6 as a remarkable activator activator of 2-deoxythioglycosides" Angew. Chem, Int. Ed, 40, No. 5, pp. 946-949, 2001.
Minotti et al., "Anthracyclines: Molecular advances and pharmacologic developments in antitumor activity and cardiotoxicity", Pharmacological Reviews. vol. 56, No. 2, pp. 185-229, 2004.
Nadas et al., "Anthracyclines as effective anticancer drugs", Expert Opin. Drug Ciscov. 1 (6), pp. 1-20.
Perez-Balderas et al., "Multivalent Neoglycoconjugates by Regiospecific cycloaddition of alkynes and azides using organic-soluble copper catalysts" Organic Letters, vol. 5, No. 11, pp. 1951-1954, 2003.
Portugal et al., "A new bisintercalating anthracycline with picomolar DNA binding affinity", J Med Chem, 48, pp. 8209-8219, 2005.
Fang et al., "Discovery of a daunorubicin analogue that exhibits potent antitumor activity and overcomes P-gp-Mediated drug resistance", J Med Chem 49, 932-941, 2006.
Zhang et al., "Synthesis and biological activity of bisdaunorubicins", Bioorganic & Medicinal Chemistry, 14, 426-434, 2006.

* cited by examiner

*Primary Examiner*—Elli Peselev
(74) *Attorney, Agent, or Firm*—Calfee, Halter & Griswold LLP

(57) ABSTRACT

Daunorubicin ("DNR") compounds synthesized with uncommon sugars exhibit enhanced effectiveness in treating various drug-resistant cancers.

18 Claims, 5 Drawing Sheets

MULTIDRUG RESISTANT ANTICANCER ANTHRACYCLINES

GOVERNMENT RIGHTS

The work described herein has been supported, at least partially, by NSF Grant CH-0316806; ACS Grant IRG-98-278-04 and a Research Starter Grant from PhRMA.

CROSS-REFERENCE TO RELATED APPLICATIONS

This application is based on Provisional Application 60/680,326 filed May 12, 2005; Provisional Application 60/703,079 filed Jul. 28, 2005; Provisional Application 60/706,688 filed Aug. 9, 2005; and Provisional Application 60/756,041 filed Jan. 4, 2006. The benefit of al these prior applications is hereby claimed. In addition, the disclosures of each of these applications, in their entireties, is incorporated herein by reference.

BACKGROUND

Anthracyclines are considered as one of the most effective anticancer drugs ever developed, either used as single agents or in combination therapy. Since the first isolation of doxorubicin (DOX) and daunorubicin (DNR) from the *Streptomycin paucities* in the 1960s, thousands of analogs have been reported. However, only a few of them have earned clinical approval, including Idarubicin (IDA, Zavedos®), Epirubicin (EPI, Farmorubicin®), Aclarubicin, Pirarubicin (Theprubicin®), and Valrubicin (Valstar®).

These drugs are natural or semi-synthetic products with similar structures and sugar moieties. For instance, DOX and DNR share the same carbon skeleton, which contains a fused tetracyclic ring and a carbohydrate motif (daunosamine). The only difference between DOX and DNR is the side chain at C14, where DNR carries a methyl group and DOX bears a primary alcohol. Although all of these anthracyclines contain similar structures, their therapeutic applications are very different. For instance, daunorubicin and idarubicin are primarily used in leukemia and lymphoma, whereas doxorubicin and epirubicin have broader anticancer activities against leukemia, lymphomas, and a variety of solid tumors including breast cancer, small cell lung cancer, cervical cancer, as well as head and neck cancer.

Although anthracyclines are widely used clinically in cancer therapy, drug resistance and cardiotoxicity limit their clinical application.

Although many mechanisms have been considered for the anticancer activity of anthracyclines, mammalian topoisomerases (specifically Top1 & Top2) are considered to be the primary molecular targets. Top1 & Top2 are ubiquitous enzymes that manage the topology of DNA during DNA replication, transcription, recombination, and chromatin remodeling. Mammalian Top1 is a single subunit enzyme that remains attached to the DNA by a tyrosyl linkage to a 3' phosphate during the DNA strand-passing step of the reaction. In contrast, mammalian Top2 is a two subunit enzyme that introduces a transient, staggered dsDNA break into a DNA duplex, and passes another dsDNA through the break. The two subunits of Top2 are covalently attached to the DNA by tyrosyl linkages to 5' phosphates during the strand-passing event.

Anthracyclines are generally believed to be Top2 poisons. Some reports have demonstrated that some anthracyclines also target Top 1.

Drug resistance of anthracyclines in cancer therapy is generally considered to be mediated by P-gp that is encoded by multidrug resistant gene (MDR1). P-gp is over-expressed in many drug-resistant cancer cells to actively export anthracyclines out of cancer cells, reduce intracellular drug concentration, and thus induce drug resistance in leukemia and solid tumors. Modification of the structure of anthracycline has demonstrated some success in overcoming drug resistance.

SUMMARY OF THE INVENTION

In accordance with the invention, it has been found that effectiveness of certain anthracycline compounds in treating various kinds of cancer can be significantly enhanced by formulating the compounds with modified sugar moieties.

Thus, the present invention provides new anthracycline compounds having the formula

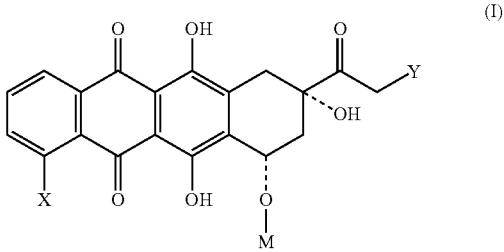

(I)

wherein X is selected from H and OMe;

Y is selected from H and OH; and

M is a mono or disaccharide moiety in which the proximal saccharide group is substituted with a single azido group or triazole group substituted with a $C_1$-$C_{10}$ alkyl, or at least one of H, Me, OH, and OMe, with the proviso that if the proximal saccharide group contains neither azido nor triazole then its 3' position cannot be substituted solely with OH, and wherein the terminal saccharide group in the case where M is a disaccharide is substituted with one or more of H, Me, OH, OMe, $NH_2$, NHMe, $NMe_2$ and $N_3$.

In this context, "single" in connection with the azido and triazole groups means that the proximal saccharide group is substituted with only one azido or triazole group independent of the other substituents on this saccharide group.

In addition, the present invention provides a new method for treating various cancers in which a therapeutically effective amount of one or more these compounds, including pharmaceutically acceptable salts thereof, is administered to a subject in need of such treatment.

Similarly, the present invention also provides a technique for reducing the cardiotoxicity and/or the multi-drug resistance (MDR) of anthracycline anticancer drugs generally, thereby enhancing the cancer-treating effectiveness of these drugs, by replacing their sugar moieties with a new class of sugar moieties having different structures than used in the past.

BRIEF DESCRIPTION OF THE DRAWINGS

The present invention may be more readily understood by reference to the following drawings wherein.

DETAILED DESCRIPTION

Figure 1A:
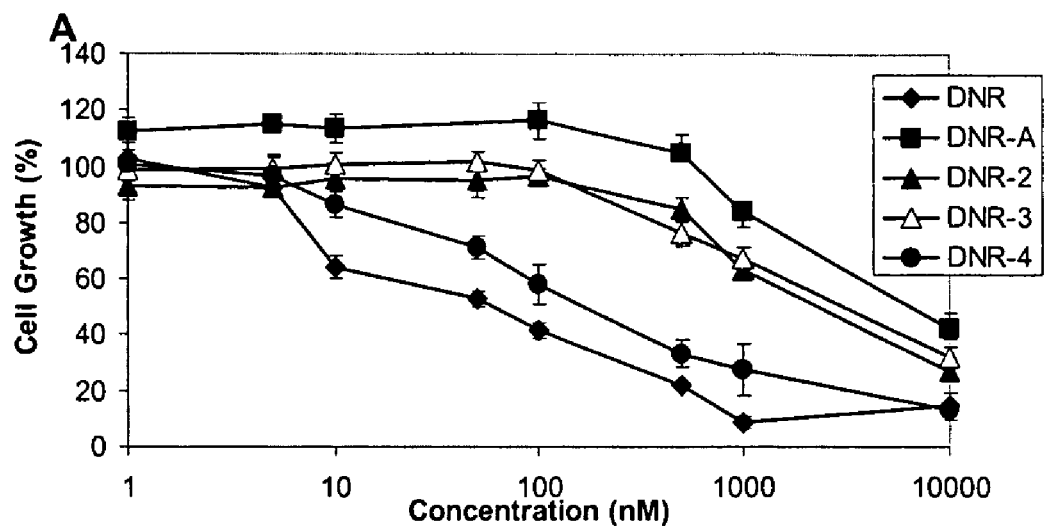
FIGS. 1A and 1B graphically illustrate the cytotoxicity of certain compounds of the present invention when tested against a particular colon cancer cell line.

In accordance with the present invention certain synthetic anthracycline compounds, which can be regarded as analogues of daunorubicin ("DNR") and doxorubicin ("DOX") with uncommon sugars, show enhanced activities in the treatment of a variety of different cancers. These uncommon sugars may be either monosaccharides or disaccharides in which the proximal saccharide group is substituted with an azido group, an alkyl triazole group or multiple Me, OH and OMe groups in combinations different from those of known doxorubicin and daunorubicin compounds.

As used herein, "treating" means curing, ameliorating or tempering the severity of the cancer or the symptoms associated therewith. The terms "treating," "treatment," and "therapy" as used herein refer to curative therapy, prophylactic therapy, and preventative therapy.

"Preventing" or "prevention" means preventing the occurrence of the cancer, or tempering the severity of the cancer if it is develops subsequent to the administration of the instant compositions. This preventing the onset of a clinically evident unwanted cell proliferation altogether or preventing the onset of a preclinically evident stage of unwanted rapid cell proliferation in individuals at risk. Also intended to be encompassed by this definition is the prevention of metastatis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject having a neoplasia, such as cancer or precancer. For methods of prevention the subject is any human or animal subject, and in certain embodiments is a human subject who is at risk of developing a cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. According to some embodiments, subject means a human.

The agents of the present invention may be administered orally, intravenously, intranasally, intraperitoneally, subcutaneously, rectally, or by any means which delivers an effective amount of the active agent to the tissue or site to be treated. It will be appreciated that different dosages may be required for treating different disorders. An effective amount of an agent is that amount which causes a statistically significant decrease in neoplastic cell count, growth, or size. Neoplastic disorders responsive to the agents of the present invention include, but are not limited to, breast cancer.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg per dose.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, etc.

Also included in the family of modified doxorubicin and daunorubicin compounds of the present invention are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other neoplasias by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art.

About 0.1 to 1000 mg of a therapeutic compound or mixture of compounds employed in the methods of the invention, or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions can be formulated in a unit dosage form, each dosage containing from about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds employed in the methods of the invention are mixed with a suitable pharmaceutically acceptable carrier. Upon mixing or addition of the compound(s), the resulting mixture may be a solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds in the methods provided herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions. As noted above, the compounds—be it polynucleotides or polypeptides—can be complexed or tagged with targeting moieties to improve their delivery.

The concentration of the compound is effective for delivery of an amount upon administration that lessens or ameliorates at least one symptom of the disorder for which the compound is administered. Typically, the compositions are formulated for single dosage administration.

The compounds employed in the methods of the invention may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions for use in the methods of the invention can be enclosed in multiple or single dose containers. The enclosed compounds and compositions can be provided in kits, for example, including component parts that can be assembled for use. For example, a compound in lyophilized form and a suitable diluent may be provided as separated components for combination prior to use. A kit may include a compound and a second therapeutic agent for co-administration. The compound and second therapeutic agent may be provided as separate component parts. A kit may include a plurality of containers, each container holding one or more unit dose of the inventive compound employed in the method of the invention. The containers can be adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The active materials can also be mixed with other active materials that do not impair the desired action, or with materials that supplement the desired action. The compounds can be used, for example, in combination with an antitumor agent, a hormone, a steroid, or a retinoid. The antitumor agent may be one of numerous chemotherapy agents such as an demethylating agent, an antimetabolite, a hormonal agent, an antibiotic, colchicine, a vinca alkaloid, L-asparaginase, procarbazine, hydroxyurea, mitotane, nitrosoureas, or an imidazole carboxamide.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

For oral administration, the pharmaceutical composition may be in the form of, for example, a tablet, capsule, suspension or liquid. The pharmaceutical composition is made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is in certain embodiments isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Where administered intravenously, suitable carriers include, but are not limited to, physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known in the art.

The compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds and methods can be used to inhibit neoplastic cell proliferation in an animal. The methods comprise administering to an animal having at least one neoplastic cell present in its body a therapeutically effective amount of at least one of the compounds, in compositions as described above. The animal can be a mammal, including a domesticated mammal. The animal can be a human.

It should be apparent to one skilled in the art that the exact dosage and frequency of administration will depend on the particular compounds employed in the methods of the invention administered, the particular condition being treated, the severity of the condition being treated, the age, weight, general physical condition of the particular patient, and other medication the individual may be taking as is well known to administering physicians who are skilled in this art.

Therapeutic Compositions

Turning now to the inventive compounds themselves, in a first group of these compounds, M is a monosaccharide moiety with the following structure:

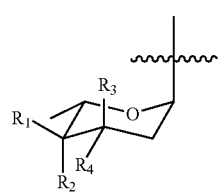

wherein $R_1$, $R_3$ and $R_4$ are independently selected from H, Me, OH and OMe, while $R_2$ is selected from H, Me, OH, OMe and $NH_3$, except that if the 3' position and the 4' position of this monosaccharide are both substituted with a single OH group, then the 2' position of this monosaccharide is also substituted with a single OH group. ("Me" in this disclosure refers to methyl.)

These compounds can be viewed as having the following structure:

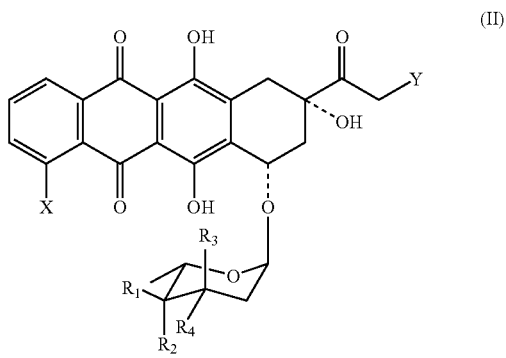

Specific compounds of this type include the following:

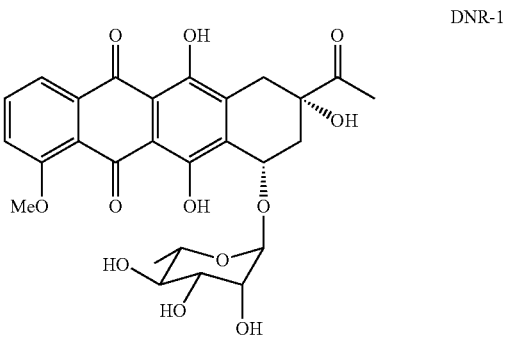

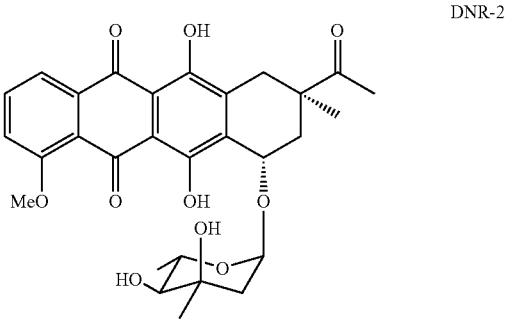

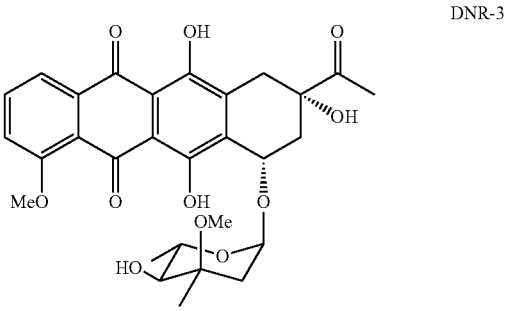

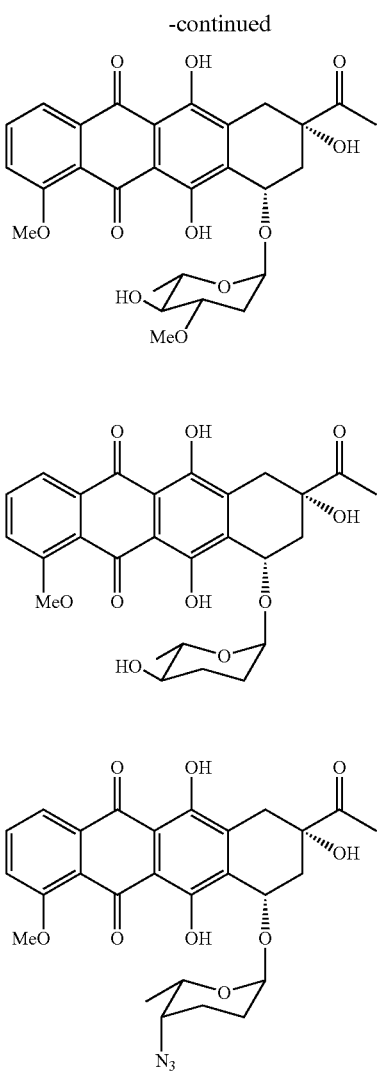

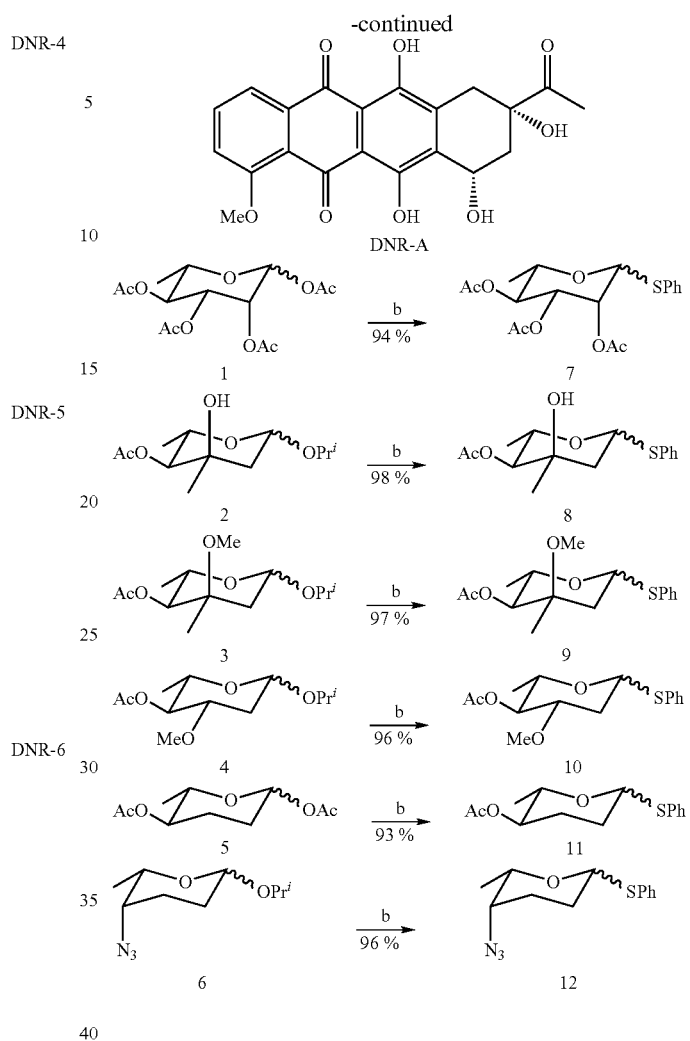

Preparation IA: Reagents and conditions: a) 0.2 M HCl, 90° C., 1 h; b) PhSH, $BF_3 \cdot Et_2O/CH_2Cl_2$, 0° C., 4 h.

These compounds can be prepared by the general method described in Lear and Hirama (Lear, M. J.; Yoshimura, F.; Hirama, M. *Angew. Chem., Int. Ed.* 2001, 40, 946-949), which is a direct and efficient α-selective glycosylation protocol for the kedarcidin sugar and L-mycarose using $AgPF_6$ as a remarkable activator of 2-deoxythioglycosides, using a promoter system comprising $AgPF_6$/TTBP (2,4,6-tert-butyl-pyrimidine). This preparation is illustrated for the six specific compounds identified above (i.e., DNR-1, 2, 3, 4, 5 and 6) as follows:

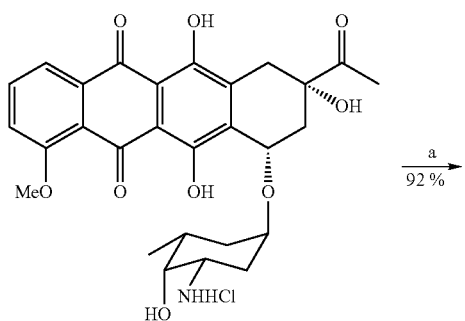

The synthesis of daunorubicin analogs starts with the preparation of the aglycon. The aglycon (DNR-A) is readily obtained from the hydrolysis of daunorubicin hydrochloride with dilute HCl at 90° C. for 1 hour. The aglycon is obtained after filtration as a red powder (Preparation IA) and is used directly for further glycosylations. The corresponding sugar donors are prepared from their corresponding precursors (compound 1-6). Acetyl group are used for protecting the hydroxyl groups present in sugar molecule, because they are cleavable under 0.1 M NaOH in THF, which allows the acid and strong base-sensitive aglycon moiety in the anthracycline not to be affected in the final deprotection procedures. As shown in Preparation I, after treatment with phenylthiol in the presence of $BF_3 \cdot Et_2O$ at 0° C. for 4 hours, the desired sugar donors (compound 7-12) are obtained in excellent yields (>94%). The thioglycosides are obtained as a mixture of α- and β-isomers. Since both isomers are able to be used for the glycosylation to produce the desired α-linked daunorubicin derivatives, separation of them is not necessary. Previous research[22] found that the tertiary hydroxyl group would not affect the further glycosylation, thus compound 2 was directly converted to the sugar donor 8. With the aglycon and the sugar donors in hand, the glycosylation was performed subsequently.

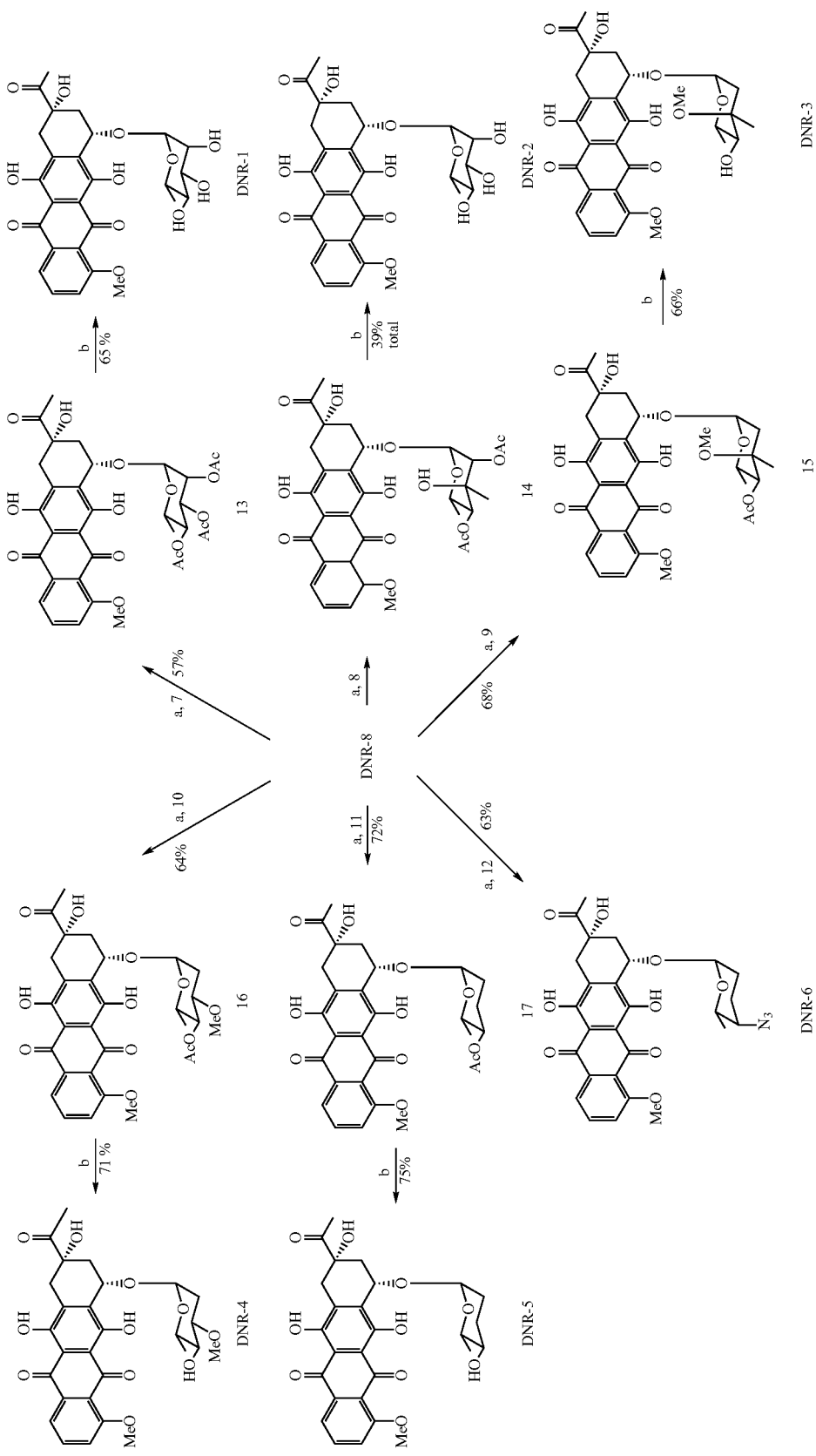

Preparation IB: Reagents and conditions: a) TTBP, AgPF$_6$CH$_2$Cl$_2$, 4 Å MS, 0° C., 4 h; b) 0.1 M NaOH/THF, 0° C., 6 h.

The mixture of aglycon (DNR-A) and sugar donor 7-12 in the presence of TTBP and 4 Å molecular sieves is treated with AgPF$_6$ at 0° C. for 4 hours to give the glycosylated products 13-17 and DNR-6 in around 60% yields. Finally, the pure DNR-2 was obtained after the deprotection step in 39% overall yield for two steps. Compound 13-17 were treated with 0.1 M NaOH for 6 hours, and the acetyl groups were successfully removed to allow the isolation of the desired DNR-1-DNR-6 in 65 to 75% yields.

The cytotoxicity of compounds DNR-1-DNR-6 prepared in this manner was examined in colon cancer cell line SW620 cells with MTS assay. 50000 cells were incubated with 0.001-10 µM DNR and its derivatives for 72 hours. Then 20 µL MTS/PMS assay solution was added to each well and the absorbance was recorded. The cell survival was calculated as percentage of cell control group without treatment. The IC$_{50}$ of all these compounds against colon cancer cell line SW620 are summarized in Table 1 and graphically illustrated in FIGS. 1A and 1B. These IC$_{50}$ values were calculated by WinNonlin 4.1 (Pharsight) from the dose-response curves of percentage of cell growth with the model: E=Emax−(Emax−E$_0$)×[C/(C+EC$_{50}$)].

TABLE 1

Cytotocicity (IC$_{50}$) of synthesized compounds against colon cancer SW620 cells.

| Compounds | DNR-1 | DNR-2 | DNR-3 | DNR-4 | DNR-5 | DNR-6 | DNR-A | DNR |
|---|---|---|---|---|---|---|---|---|
| IC$_{50}$ in SW620 (nM) | 264.6 | >1000 | >1000 | 104 | 350 | >1000 | >2000 | 33.4 |

Figure 1B:
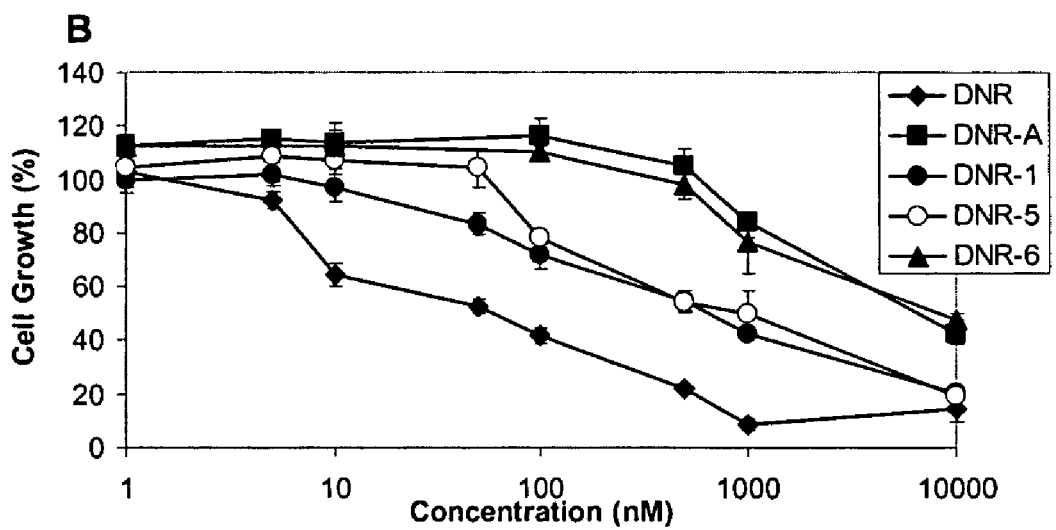

The results in Table I and FIGS. 1A and 1B show that the aglycon DNR-A exhibited 70- to 100-fold lower cytotoxicity than compounds DNR-1-DNR-6. This shows that the structure of the sugar moiety in daunorubicin plays a critical role in determining its anticancer activity.

Compound DNR-4 with 3'-OMe terminal 2,6-dideoxy sugars showed very potent cytotoxicity with IC$_{50}$ of 104 nM. See, FIG. 1A. Importantly, compared to compounds DNR-2 and DNR-3 (with axial-3'-OMe or axial-3'-OH group), DNR-4 (with an equatorial-3'-OMe group) showed 10 to 20-fold higher anticancer activity. This suggested that the axial-3'-substitutent in sugar (such as in compounds DNR-2 and DNR-3) may interfere daunorubicin binding to DNA.

Compounds DNR-1 and DNR-5 with equatorial-4'-OH showed similar activity, while DNR-6 (substituted 4'-OH with axial-4'-N$_3$ in the sugar moiety), which is similar to aglycon DNR-A, lost its cytotoxicity (FIG. 1B). This suggests that 4-OH in the sugar may also be important for sugar containing anthracycline as an anticancer agent.

The IC$_{50}$ values of DNR-1, DNR-4, DNR-5 and DNR-6 showed that compound DNR-4 has the best activity followed by DNR-1, DNR-5, and DNR-6. This tendency suggested that the 2,6-dideoxy sugars are the best choice for making biological active daunorubicin analogs than 6-deoxysugars, 2,3,6-trideoxysugars, or 2,3,4,6-tetradeoxysugars.

In the second group of the inventive compounds, the sugar moiety has the following structure:

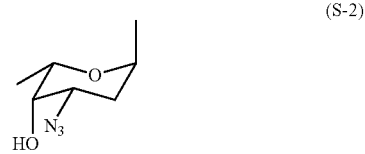

(S-2)

This compound, which is occasionally referred to herein as "ADNR," can be viewed as having the following structure:

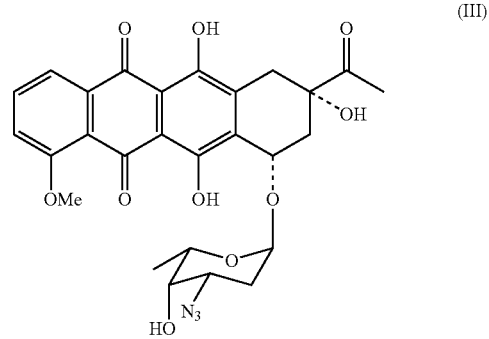

(III)

This compound can be readily prepared by treatment of DNR with a TfN$_3$ solution according to the method described in Alper, P. B.; Hung, S.-C.; Wong, C.-H., Metal Catalyzed Diazo transfer for the Synthesis of Azides from Amines. *Tetrahedron Lett.* 1996, 37, 6029-6032.

In the third group of the inventive compounds, the sugar moiety has the following structure:

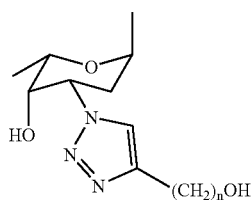

(S-3)

wherein n=1, 2, 3 or 4; and

These compounds, which are occasionally referred to herein as "ADNR" and "A1"-"A4" can be viewed as having the following structure:

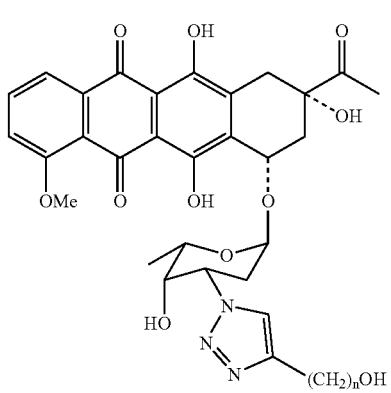

(IV)

These compounds can be prepared the Huisgen 1,3-dipolar cycloaddition using $(EtO)_3PCuI/DIPEA$ as a catalyst. See, Perez-Balderas, F.; Ortega-Munoz, M.; Morales-Sanfrutos, J.; Hernandez-Mateo, F.; Calvo-Flores, F. G.; Calvo-Asin, J. A.; Isac-Garcia, J.; Santoyo-Gonzalez, F., Multivalent Neoglycoconjugates by Regiospecific Cycloaddition of Alkynes and Azides Using Organic-Soluble Copper Catalysts, *Organic Lett.* 2003, 5, 1951-1954.

As indicated above, drug resistance in leukemia and solid tumors is believed due at least in part to overexpression of P-gp, which in turn causes therapeutic anthracyclines to be actively exported out of the cancer cells. To determine the resistance of the compounds of Formula (III) to this phenomenon, the P-gp export of these compounds was tested against DNR as a control in drug-resistant leukemia cells (K562/Dox) in the presence or absence of a P-gp inhibitor (cyclosporine, CsA). Since P-gp is significantly overexpressed in drug-resistant K562/Dox cancer cells, these cells provide good models for P-gp-mediated drug resistance study.

These tests revealed that, in the absence CsA (the P-gp inhibitor), DNR, readily diffused into the K562/Dox cells after 30 min of incubation and then were readily exported out of the cells due to the P-gp in the cell membrane. However, when CsA (5 μM) was co-incubated with DNR for 30 min, much more drug was accumulated in the cells (uptake phase) as measured by FACS. In addition, the P-gp inhibitor (CsA) significantly inhibited the drug efflux and increased drug accumulation in the cells. This confirms that DNR is a substrate of P-gp, and inhibition of P-gp increases intracellular DNR accumulation.

In contrast, the new anthracycline analogs (ADNR and A1-A4) were also readily diffused into K562/Dox cells. However, the P-gp inhibitor (CsA) did not show any effect on the retention of these new compounds in both uptake and efflux phases in the cancer cells. These results strongly suggest that modifications of the sugar structures of DNR in these new compounds avert P-gp binding, diminish the drug efflux, and may well overcome P-gp-mediated drug resistance.

Figure 2A:
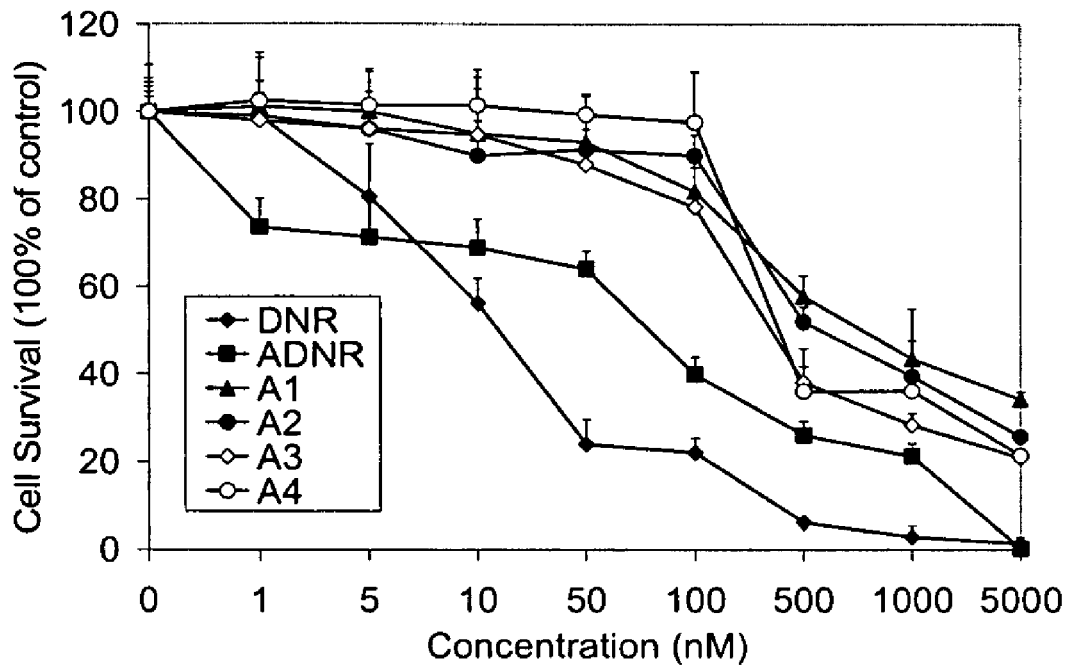
FIGS. 2A and 2B graphically illustrate the cytotoxicity of certain compounds of the present invention when tested against a particular line of leukemia cells.
Figure 2B:
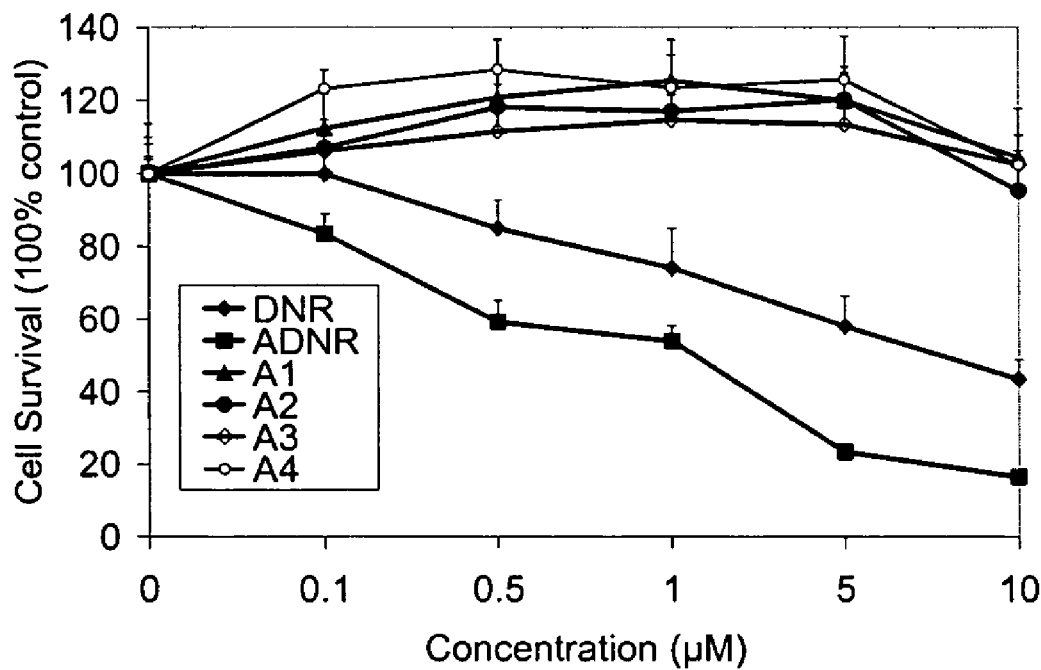

New compounds ADNR and A1-A4 were also tested to determine if they could overcome drug resistance by measuring their cytotoxicity in drug-resistant leukemia cells (K562/Dox) by MTS assay in comparison with DNR. The results are shown in FIGS. 2A and 2B. As shown in these figures, DNR showed much higher $IC_{50}$ (>5 μM) against K562/Dox cells than that against K562 (15 nM). The drug resistance index (DRI, ratio of $IC_{50}$ in drug-resistant cells over $IC_{50}$ in drug-sensitive cells) is a good indicator of drug's ability to overcome resistance. The DRI for DNR is more than 333. This data strongly suggests that K562/Dox cells are resistant to DNR, which is due to the drug efflux by P-gp as measured by FACS. In contrast, ADNR exhibited potent anticancer activity with $IC_{50}$ of 0.075 μM in drug-sensitive K562, and 1.0 μM in drug-resistant cells. Compared to DNR, ADNR was less active in drug-sensitive K562, however, ADNR was at least 5-fold more active than DNR against drug-resistant K562 cells. Its DRI is only 13, which is 25-fold lower than that of DNR. These data indicate that ADNR overcomes P-gp-mediated drug resistance.

Compounds A1-A4, however, showed much less activity in both drug-sensitive and drug-resistant K562 cells.

Figure 3:
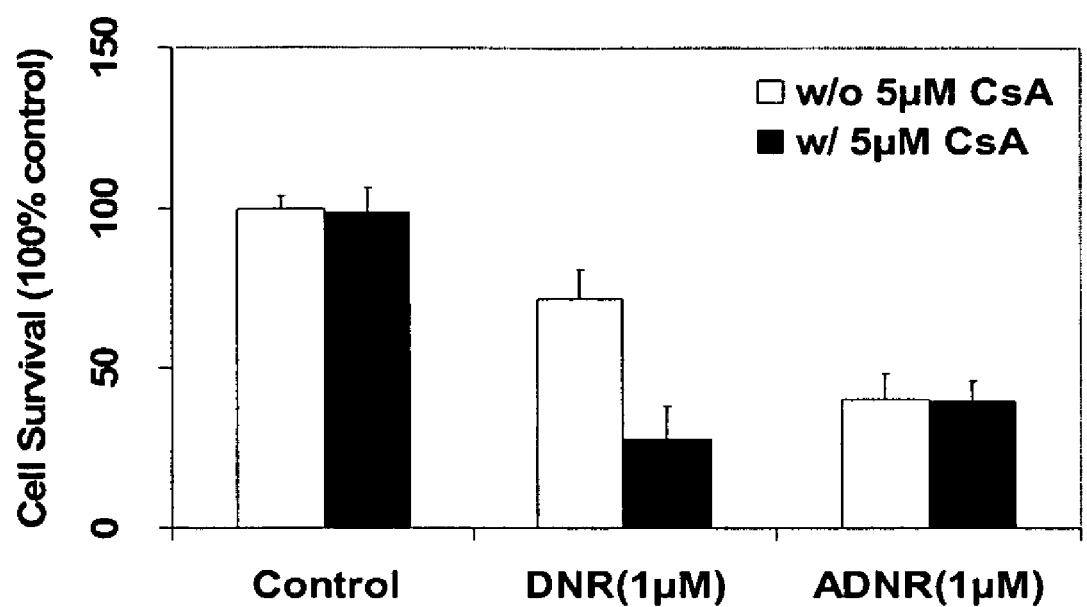
FIG. 3 graphically illustrate the cytotoxicity of still other compounds of the present invention when tested against a particular line of leukemia cells.

To further confirm that drug resistance to DNR is partially due to P-gp efflux and that ADNR can avert P-gp recognition, we tested cytotoxicity of DNR and ADNR against K562/Dox in the presence of a P-gp inhibitor (CsA). The results are shown in FIG. 3. As shown in this figure, CsA alone (5 μM) did not show any cytotoxicity to K562/Dox, while DNR (1 μM) alone showed 30% cell killing effect; however, the combination of CsA and DNR showed more than 70% cell killing effects under the same condition. This indicates that CsA inhibits P-gp for drug efflux and increases DNR intracellular concentration for better cytotoxicity. However, ADNR at 1 μM concentration kills more than 50% of the cancer cells, and CsA did not change the cell killing effects of ADNR. This further confirms that ADNR is no longer a P-gp substrate, thus overcoming P-gp-mediated drug resistance.

Figure 4:
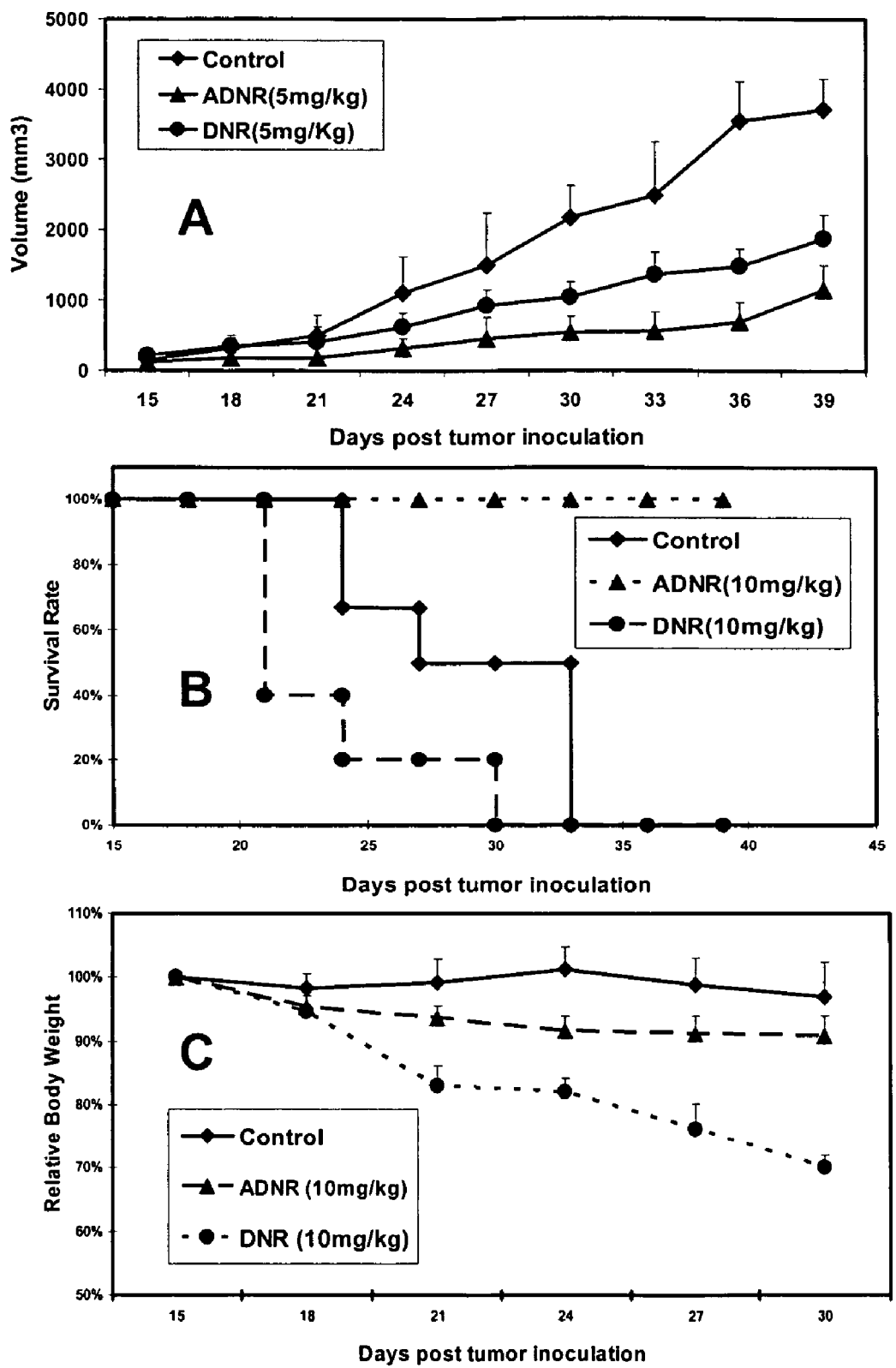
FIGS. 4A, 4B and 4C graphically illustrate the cytotoxicity of the compounds of FIG. 3 against leukemia cells as determined by certain in vivo testing.

Based on the above in vitro data, the anticancer activity of ADNR was evaluated against drug-resistant cancers in the xenograft mouse model. In this animal model, $10^7$ drug-resistant leukemia K562/Dox was injected subcutaneously into nude mice. After 14 days, the tumor reached 100 $mm^3$. From day 15, ADNR (5 or 10 mg/kg) and DNR (5 or 10 mg/kg) were injected to the mice intraperitoneally twice per week for three weeks. The tumor volume was measured every three days. The results are shown in FIGS. 4A, 4B and 4C. As shown in these figures, tumor growth was very rapid in the control group (without drug treatment). However, ADNR and daunorubicin (DNR) significantly inhibited tumor growth one week after dose, while ADNR (5 mg/kg) showed a 2.5-fold higher maximum growth inhibition rate against drug-resistant cancers than DNR. This result indicates that ADNR is more effective than DNR against drug-resistant cancers.

When ADNR and DNR were given to the xenograft model at the maximum tolerable dose of 10 mg/kg twice per week for three weeks, body weight of DNR treated mice decreased more than 70% and all of them died after two weeks of DNR treatment, while the ADNR treatment group and control group did not show any significant body weight change (FIG. 4C). All animals (8/8) in ADNR group survived (100%) after 50 days, while the mice in DNR group (6/6) died before 30 days (due to both tumor growth and drug toxicity, 50% mice died before 20 days). The mice in control group (5/5) all died in 33 days (50% mice died in 25 days) (FIG. 4B). This data indicates that ADNR overcomes P-gp-mediated drug resistance and is effective in treatment of drug-resistant cancers with better safety profile in K562/Dox leukemia xenograft model.

In the fourth group of the inventive compounds, the sugar moiety has the following structure:

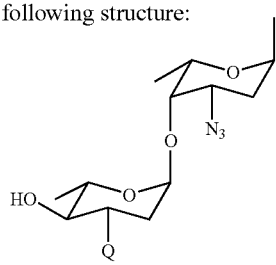

These compounds can be viewed as having the following structure

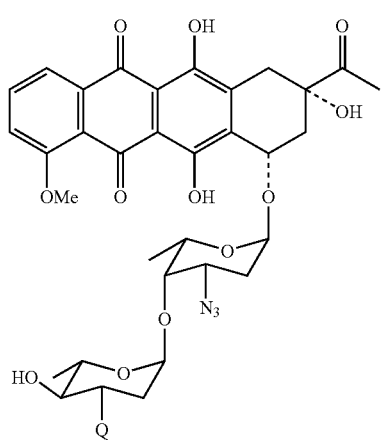

(V)

wherein Q is a single substituent selected from H, OH, OMe and N₃ or two substituents selected from Me plus OMe or Me plus OH.

In these compounds, the first sugar is an 3-azido-2,3,6-trideoxy-L-lyxo-α-hexopyranose while the second sugar, which can be selected from a series of uncommon sugars including four 2,6-dideoxy sugars and two 2,3,6-trideoxysugars, is linked via α(1→4) to the first sugar.

Specific compounds of this type include the following:

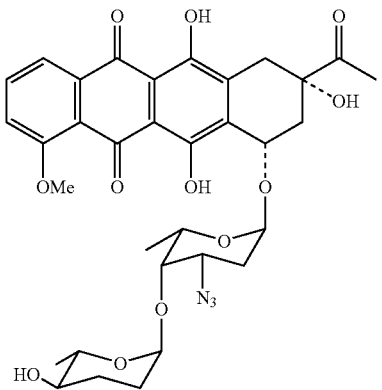

1

-continued

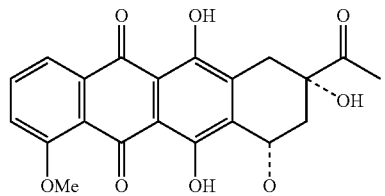

2

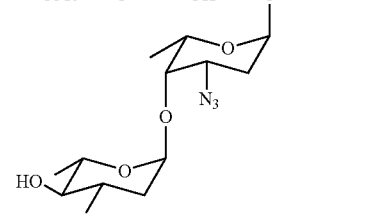

3

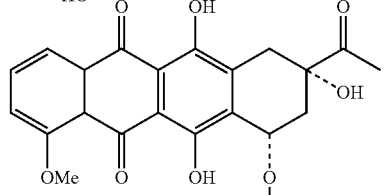

4

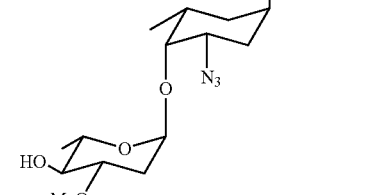

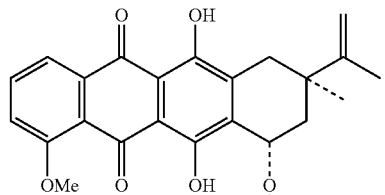

5

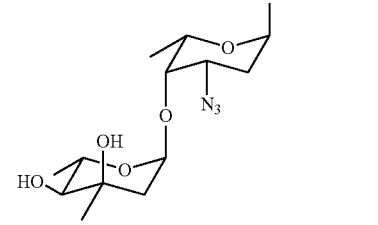

-continued

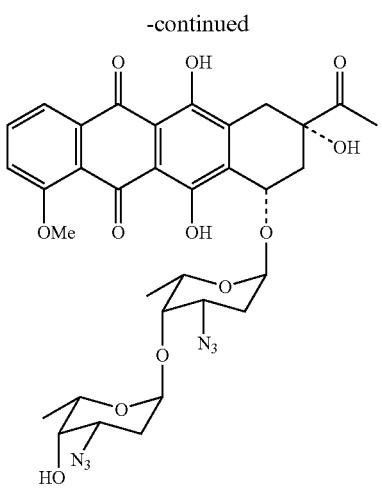

6

Two preparations can be used to synthesize these compounds. Both are based on glycosylation using the catalyst system mentioned above, AgPF$_6$/TTBP. In one preparation, which is illustrated in the following Scheme 2, the amino group of DNR is transformed into an azido group through the method of Alper & Wong o produce 3'-azido-deamino-daunorubicin (8) as a glycosyl acceptor for the glycosylation with the second 2,6-dideoxysugars. See, Alper, P. B.; Hung, S.-C.; Wong, C.-H., Metal catalyzed diazo transfer for the synthesis of azides from amines. *Tetrahedron Lett.* 1996, 37, (34), 6029-6032.

Scheme 2: Reagents and conditions: (a) TTBP, AgPF$_6$/CH$_2$Cl$_2$, 0° C.; (b) 0.1 M NaOH/THF, 0° C.

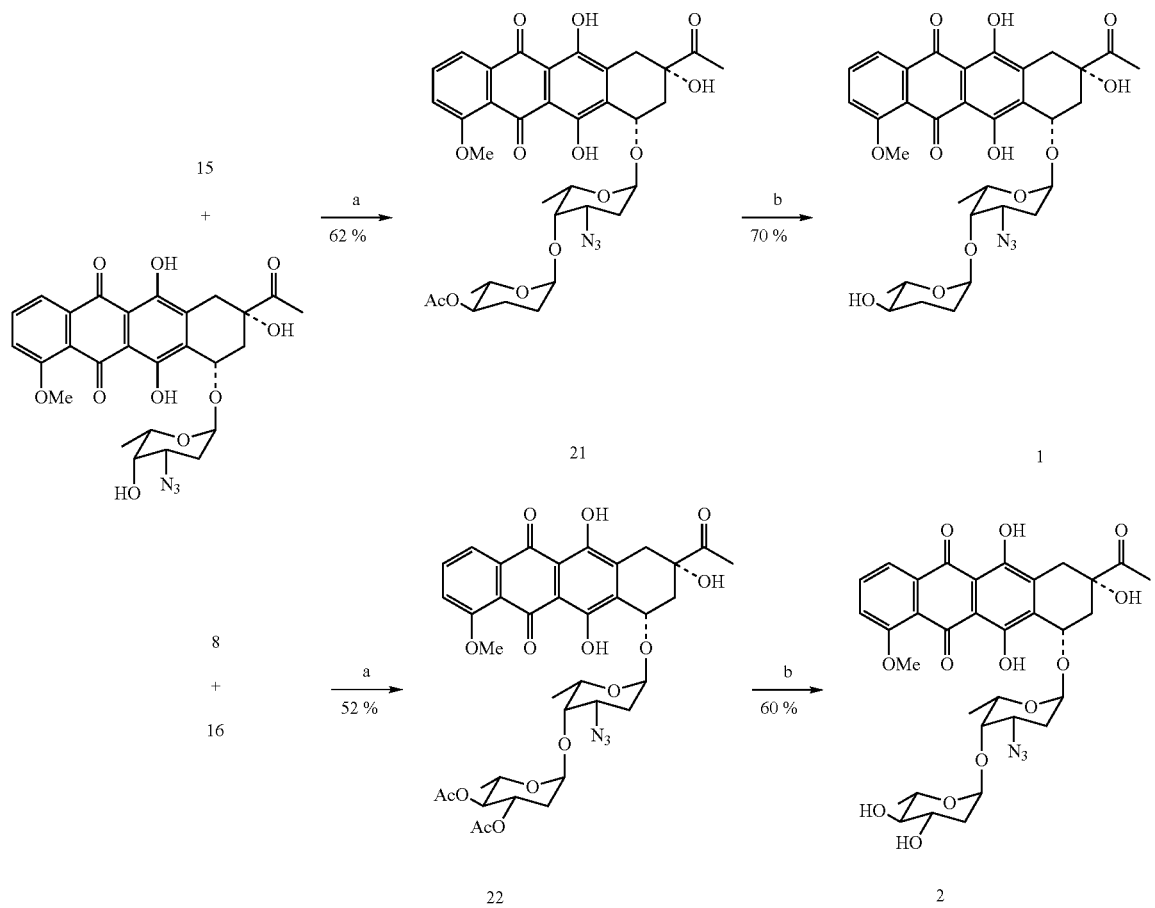

In the second preparation, 3'-N-trifluoro acetyl daunorubicin (7) is applied as the glycolsyl acceptor for the glycosylation reaction, and the amino group is converted to an azido group after glycosylation and deprotection. This preparation is illustrated in the following Scheme 3.

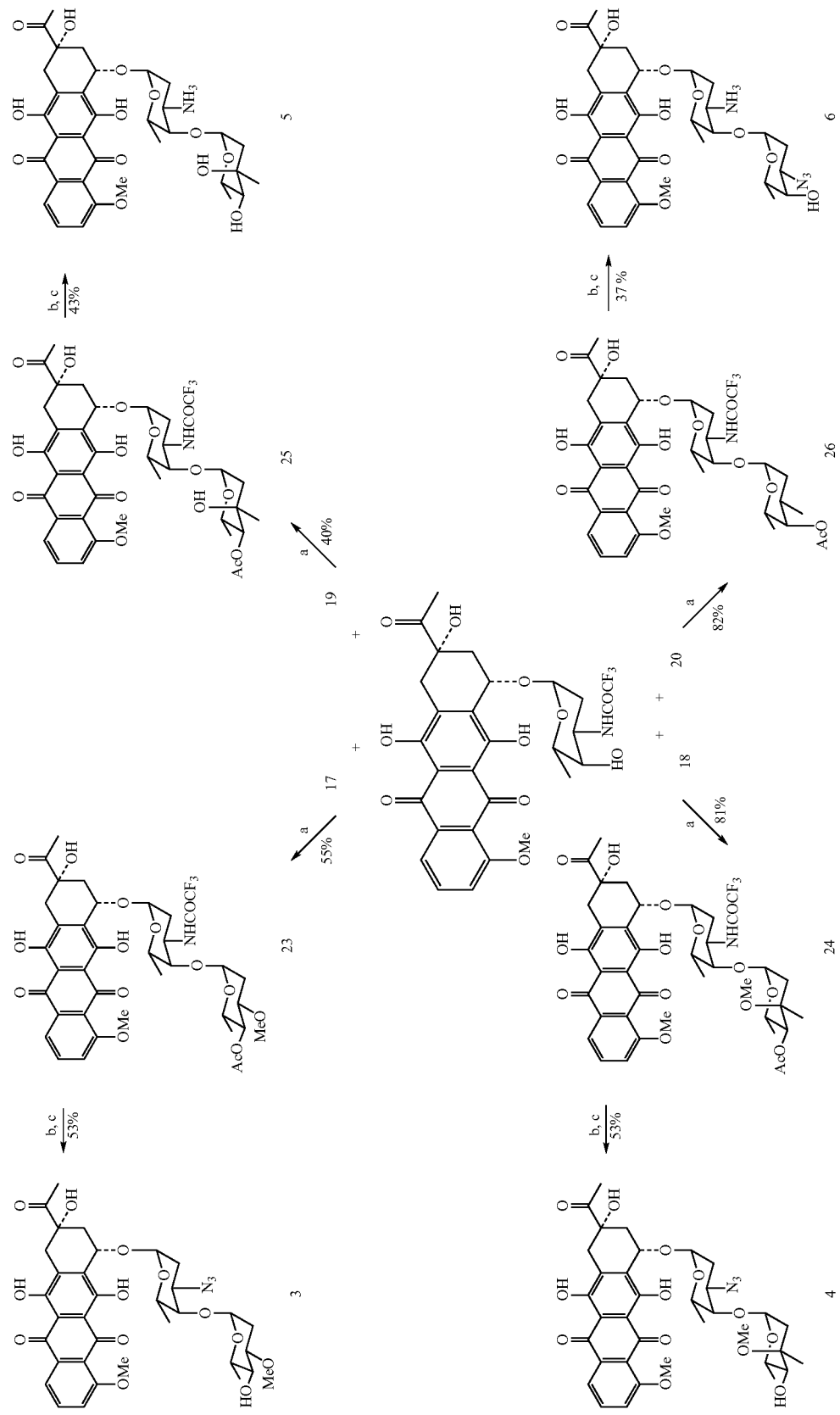
Scheme 3. Reagents and conditions: (a) TTBP, AgPF$_6$/CH$_2$Cl$_2$, 0 °C.; (b) 0.1 M NaOH/THF, 0 °C.; (c) K$_2$CO$_3$, CuSO$_4$, TfN$_3$ solution The synthetic routes of glycosyl acceptors (7 and 8) and glycosyl donors are outlined in the following Scheme 1.
Scheme 1: Reagents and conditions (a) $K_2CO_3$, $CuSO_4$, $TfN_3$ solution; (b) $(CF_3CO)_2$/pyridine, -20° C., 15 min; (c) PhSH, $BF_3Et_2O$ / $CH_2Cl_2$, 0° C., 2h.
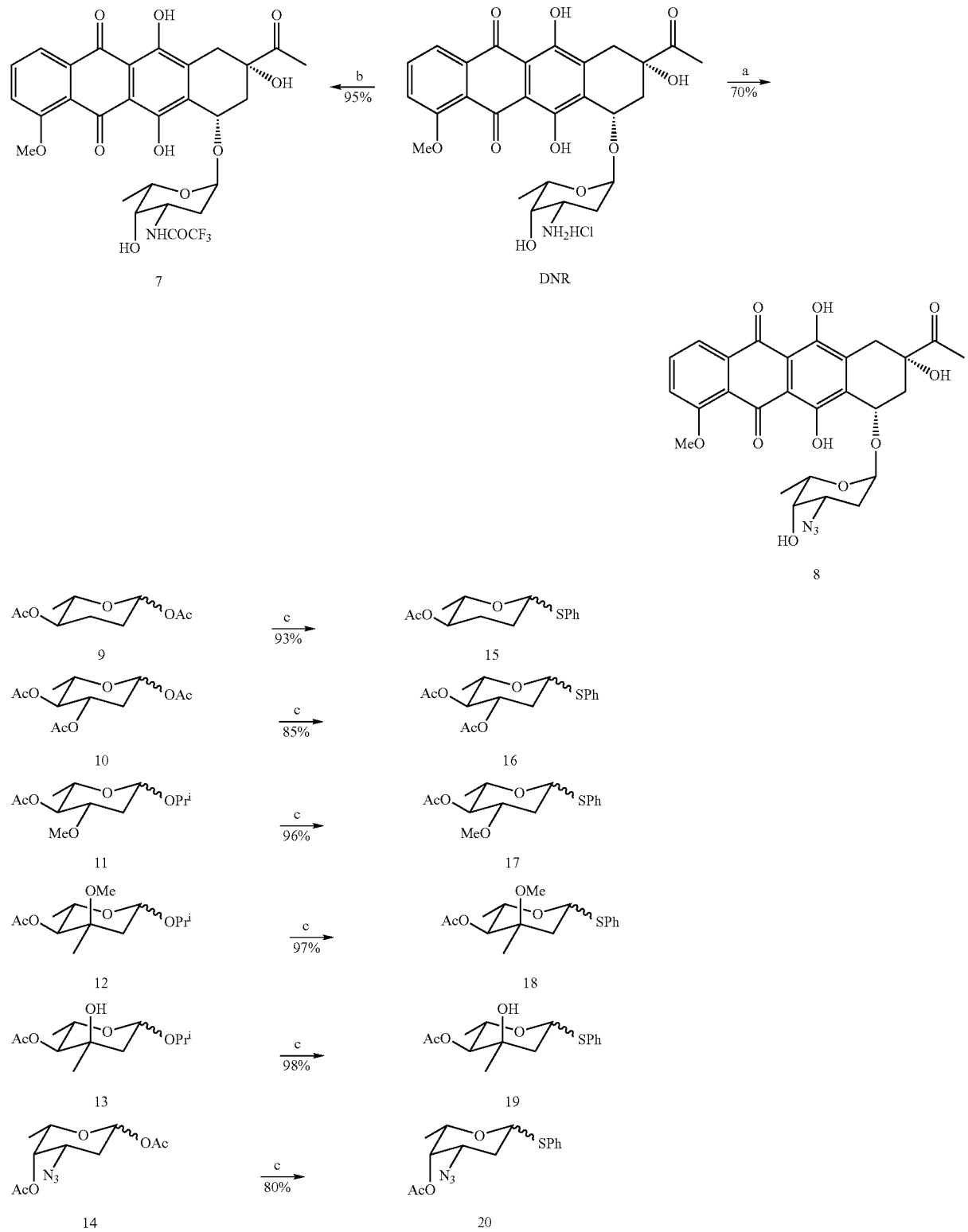

Compound 8 is readily prepared by treatment of DNR with TfN$_3$ solution in 70% yield. Treatment of DNR with trifluoroacetic anhydride in pyridine at −20° C. for 15 min gives the aglycone 7 in high yields (e.g. 95%). The corresponding glycosyl donors are prepared from their corresponding precursors (compound 9-14). The acetyl group is used for protecting the hydroxyl groups present in the sugar molecule, because they are cleavable under 0.1 M NaOH in THF, which allows the acid and strong base sensitive aglycone moiety in the anthracycline molecule not to be affected in the final deprotection manipulations. As shown in Scheme 3, after treatment with phenylthiol in the presence of BF$_3$.Et$_2$O at 0° C. for 2 hours, the desired sugar donors (compounds 15-20) are obtained in excellent yields. The thiolglycosides are obtained as a mixture of α- and β-isomers. Since both isomers are able to be used for the glycosylation to produce the desired α-linked daunorubicin derivatives, separation of them was unnecessary.

With the glycosyl acceptors and donors in hand, the glycosylation was performed subsequently. The mixture of glycosyl acceptors (7 and 8) and donors 15-20 in the presence of TTBP and 4 Å molecular sieves was treated with AgPF$_6$ at 0° C. for 2-4 h to give the products 21-26 in good yields (Scheme 2-3). Glycosylation of 8 with glycosyl donors 15 and 16 gave exclusively the α-product 21 and 22 in yields of 62% and 52%, respectively. The $^1$H NMR data indicated the desired α-linkage was formed predominantly (α:β>5:1). Mild deprotection of the ester groups with 0.1 M NaOH in THF afforded the final products 1 and 2 in yields of 70%, and 60%, respectively. Condensation of 7 with glycosyl donors 18 and 20 exclusively formed the α-products 24 and 26 with yield of 81%, and 82%, respectively. However, condensation of 7 with the glycosyl donors 17 and 19 gave the anomeric mixtures (α:γ=2:1) with yields of 83%, and 60%, respectively. After glycosylation, deprotection of the desired disaccharide intermediates 21-26 with 0.1 M NaOH in THF followed by treatment with TfN$_3$ solution in CH$_2$Cl$_2$ afforded the final compounds 3-6 with overall yields of 53%, 50%, 43%, and 37%, respectively.

Figure 5:
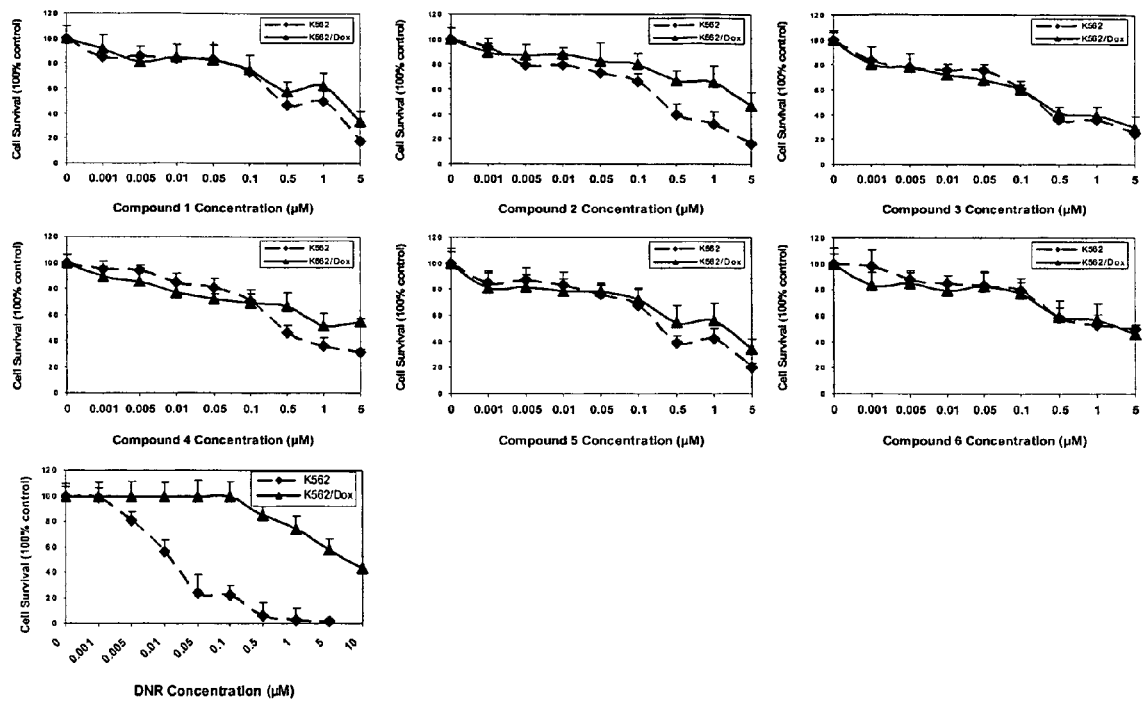
FIG. 5 graphically illustrate the cytotoxicity of still other compounds of the present invention against doxorubicin-resistant leukemia cells.

The anticancer activities of Compounds 1-6 were examined in leukemia cells K562 and doxorubicin-resistant K562/Dox cells by MTS assay. The drug-resistant K562/Dox cell line was induced by doxorubicin treatment. The cell line was cultured in 0.1 μM doxorubicin one week/per month, followed by 10 days culture without doxrubicin before experiment. This is to maintain similar high levels of P-gp expression in each experiment. In drug-resistant K562 cells, MDR1 mRNA was induced by 600-fold higher than drug-sensitive K562 cells as measured by real-time PCR (data not shown). The 2000-10000 cells were incubated with 0.001-5 μM DNR and its derivatives for 72 hours. Then 20 μL MTS/PMS assay solution was added to each well and the absorbance was recorded. The cell survival was calculated as percentage of cell control group without treatment. The anticancer activities are summarized in Table 2 and graphically illustrated in FIG. 5. The IC$_{50}$ values were calculated by WinNonlin 4.1 (Pharsight) from the dose-response curves of percentage of cell growth with the model: $E=Emax-(Emax-E_0)\times[C/(C+EC_{50})]$

TABLE 2

| Compounds | Cytotoxicity (IC$_{50}$) and Drug Resistance Index (DRI) of Disaccharide Daunorubicins and DNR. | | | | | | | |
|---|---|---|---|---|---|---|---|---|
| | 1 | 2 | 3 | 4 | 5 | 6 | 8 | DNR |
| IC$_{50}$ in K562 (μM) | 0.787 | 0.287 | 0.278 | 0.225 | 0.448 | 1.132 | 0.075 | 0.015 |
| IC$_{50}$ in K562/Dox (μM) | 1.926 | 5.437 | 0.289 | 12.070 | 1.628 | 6.388 | 1 | >5 |
| DRI | 2.45 | 18.94 | 1.04 | 53.64 | 3.63 | 5.64 | 13.3 | >333 |

In drug-sensitive cells, compounds 1-6 were found to be active against leukemia K562 cells with IC$_{50}$ values in the nanomolar range (200-1100 nM), yet their IC$_{50}$ values are higher than that of parent compound DNR (15 nM). Compounds 2-5 with 2,6-dideoxy sugars showed 3 to 4-fold better activity than compounds 1 and 6 with 2,3,6-trideoxy sugars. These results indicate that 2,6-dideoxy sugars are the best choice to modify the sugar chain of disaccharide anthracyclines compared with 2-deoxy-, 6-deoxy-, and 2,3,6-trideoxy sugars.

In doxorubicin-resistant K562/Dox cells, compounds 1, 3 and 5 exhibit much better activities (with IC$_{50}$ value in 0.29-2.0 μM) than DNR (with IC$_{50}$ value of larger than 5 μM). The drug resistance index (DRI, ratio of IC$_{50}$ in drug-resistant cells over IC$_{50}$ in drug-sensitive cells) is a good indicator of drug's ability to overcome resistance. The smaller DRI indicates better capacity to overcome drug resistance. As summarized in Table 2, DRI values of compounds 1-6 were 6.2 to 320-fold lower than that of DNR with a value of 333. In comparison, monosaccharide daunorubicin with 3-azido sugar (compound 8) also showed strong cytotoxicity against drug-resistant K562 with DRI of 13.3 (Table 2). Among the synthesized compounds, compound 3 emerged as the most active compound against drug-resistant cells with at least 17-fold higher activity than DNR. It completely overcomes the drug-resistance in this leukemia cell line (DRI=1.04, 320-fold lower than that of parent compound DNR). It is worthy to be further evaluated as a new drug candidate.

Compounds 2 with a 3"-equatorial hydroxyl group and 3 with a 3"-equatorial methoxyl group possess similar sugar moieties and showed similar activity in drug-sensitive cells. However, compound 3 exhibited 18-fold higher activity than that of compound 2. The substitution of hydrogen atom in the equatorial 3-OH group of the second sugar with methyl group resulted in significant increase of activity against drug-resistant cells. On the contrary, compound 5 with a 3"-axial hydroxyl group exhibited 14-fold higher activity against drug-resistant K562 than that of compound 4 with a 3"-axial methoxyl group. This suggests that the substitution and orientation of the 3-OH group in the second sugar may significantly influence its binding to P-gp and activity against drug-resistant cells.

From the above, it can be seen that the present invention provides a new method for treating various cancers in which a therapeutically effective amount of one or more compounds described above, including pharmaceutically acceptable salts thereof, is administered to a subject in need of such treatment. In particular, the present invention provides a technique for reducing the cardiotoxicity and/or the multi-drug resistance (MDR) of anthracycline anticancer drugs generally, thereby enhancing the cancer-treating effectiveness of these drugs, by replacing their sugar moieties with a new class of sugar moieties having different structures than used in the past. In some embodiments, the present invention provides methods and compositions for treating subjects whose cancer(s) has/have developed resistance to one or more chemotherapeutic agents.

Although the compounds of this invention, have been shown to be particularly effective in connection with treating leukemia and colon cancer, they are expected to be similarly effective in treating other forms of cancers currently being treated with anthracycline anticancer drugs including various lymphomas as well as various solid tumor cancers including breast, small cell lung, cervical, head and neck cancers. Other forms of cancer such as cancers of the breast, uterine, ovarian, cervical, colon, rectal, stomach, thyroid, lung, testicular, kidney, bladder, trachea, small intestine, vulva, liver, pancreatic and prostate should also be treatable with the compounds of this invention.

The invention claimed is:

1. An anthracycline compound, including a pharmaceutically acceptable salt thereof, having a formula:

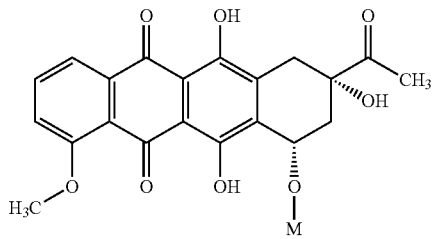

wherein M is selected from:

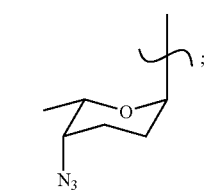
(a)

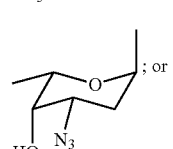
(b)

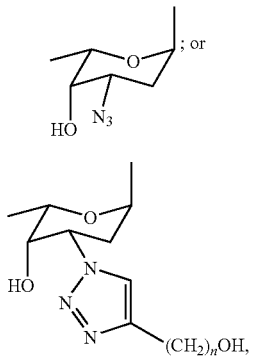
(c)

wherein n=1, 2, 3 or 4.

2. An anthracycline compound, including a pharmaceutically acceptable salt thereof, having a formula selected from the following formulas:

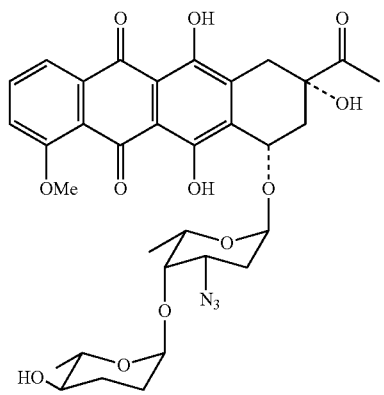
1

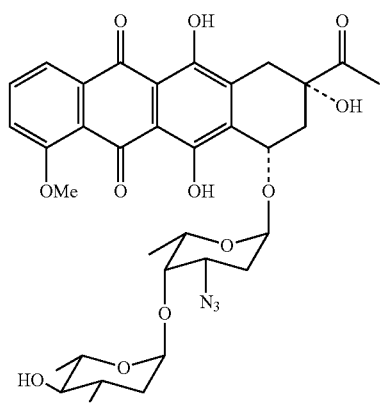
2

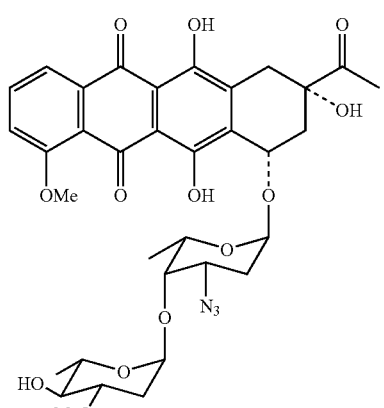
3

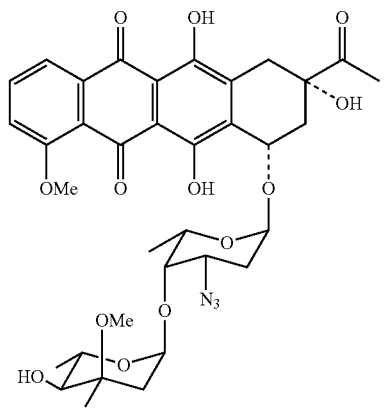
4

-continued

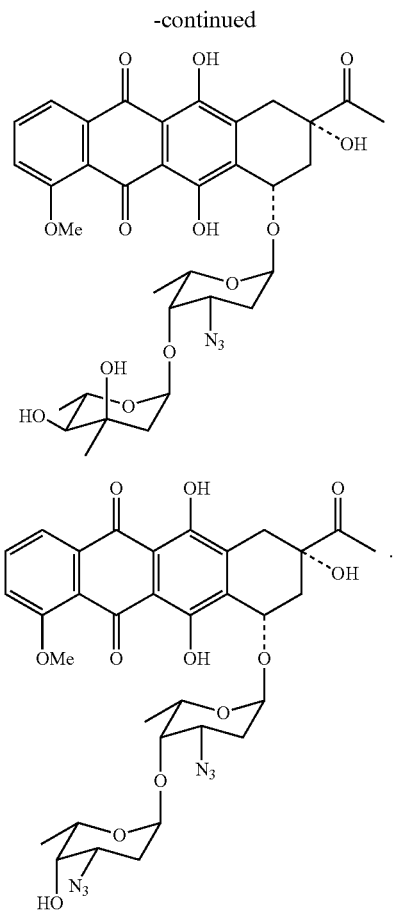

3. A method for treating ameliorating or tempering the severity of cancer in a subject, the method comprising administering a therapeutically effective amount of the anthracycline compound of claim 1 to the subject, wherein the cancer is selected from the group consisting of leukemia and lymphoma.

4. A method for ameliorating or tempering the severity of cancer in a subject, the method comprising administering a therapeutically effective amount of the anthracycline compound of claim 2 to the subject, wherein the cancer is selected from the group consisting of leukemia and lymphoma.

5. The method of claim 3, wherein the cancer is a leukemia.

6. The method of claim 4, wherein the cancer is a leukemia.

7. The method of claim 3 wherein the subject is a human subject.

8. The method of claim 4 wherein the subject is a human subject.

9. A formulation for ameliorating or tempering the severity of cancer in a subject having cancer comprising the anthracycline compound of claim 1, wherein the cancer is selected from the group consisting of leukemia and lymphoma.

10. The formulation of claim 9 further comprising a carrier.

11. A formulation for ameliorating or tempering the severity of cancer in a subject having cancer comprising the anthracycline compound of claim 2, wherein the cancer is selected from the group consisting of leukemia and lymphoma.

12. The formulation of claim 11 further comprising a carrier.

13. A method for ameliorating or tempering the severity of cancer in a subject who has developed chemoresistance to a formulation comprising one or more chemotherapeutic agents, the method comprising administering the formulation to the subject, wherein one or more of the chemotherapeutic agents are replaced with the anthracycline compound of claim 1, and further wherein the cancer is selected from the group consisting of leukemia and lymphoma.

14. The method of claim 13 wherein the cancer is leukemia.

15. A method for treating ameliorating or tempering the severity of cancer in a subject who has developed chemoresistance to a formulation comprising one or more chemotherapeutic agents, the method comprising administering the formulation to the subject, wherein one or more of the chemotherapeutic agents are replaced with the anthracycline compound of claim 2, and further wherein the cancer is selected from the group consisting of leukemia and lymphoma.

16. The method of claim 15 wherein the cancer is leukemia.

17. A method for preparing the anthracycline compounds of claim 1 comprising the steps of:
   1) deglycosylating daunorubicin or a salt thereof, and
   2) reglycosylating of the 10-hydroxy position of the deglyclosylated daunorubicin with a glycoside M of claim 1.

18. A method for preparing the anthracycline compounds of claim 2 comprising the steps of:
   1) deglycosylating daunorubicin or a salt thereof, and
   2) reglycosylating of the 10-hydroxy position of the deglycosylated daunorubicin with a disaccharide consisting of a 3-azido-2,3,6-trideoxy-L-lyxo-α-hexopyranose linked α(1→4) to a 2,6-dideoxy hexopyranose or a 2,3,6-trideoxy hexopyranose.

* * * * *